United States Patent [19]

Takahashi et al.

[11] 4,187,486
[45] Feb. 5, 1980

[54] OXYGEN CONCENTRATION DETECTING ELEMENT AND METHOD OF PRODUCING THE SAME

[75] Inventors: Hideaki Takahashi, Aichi; Takashi Takeuchi, Nagoya, both of Japan

[73] Assignee: Kabushiki Kaisha Toyota Chuo Kenkyusho, Aichi, Japan

[21] Appl. No.: 898,372

[22] Filed: Apr. 20, 1978

[30] Foreign Application Priority Data

Apr. 20, 1977 [JP] Japan .................................. 52-45589

[51] Int. Cl.² .................................. H01L 49/00; H01B 1/02
[52] U.S. Cl. .................................. 338/34; 252/514; 23/232 E; 422/98
[58] Field of Search .................................. 252/514; 338/34; 23/232 E; 422/98; 73/27 R

[56] References Cited

U.S. PATENT DOCUMENTS

| 3,607,084 | 9/1971 | Mackey | 73/27 R X |
| 3,865,550 | 2/1975 | Bott et al. | 338/34 X |
| 4,000,089 | 12/1976 | Senda | 252/514 |
| 4,007,435 | 2/1977 | Tien | 338/34 |

FOREIGN PATENT DOCUMENTS 51-100796 6/1976 Japan.

*Primary Examiner*—Benjamin R. Padgett
*Assistant Examiner*—E. Suzanne Parr
*Attorney, Agent, or Firm*—Oblon, Fisher, Spivak, McClelland & Maier

[57] ABSTRACT

This invention provides an oxygen concentration detecting element and method of producing the same for use in detecting the oxygen concentration of gases such as exhaust gases from gasoline engines. The oxygen concentration detecting element is characterized by a shaped and sintered porous body consisting essentially of semiconductor materials and platinum particles dispersed at an average particle-to-particle spacing of no more than 10 μ throughout said element.

The element has high durability and non-hysteresis characteristics, and can be used over a wide temperature range. The element is especially useful in detecting the oxygen concentration of an exhaust gas.

17 Claims, 16 Drawing Figures

OXYGEN CONCENTRATION DETECTING ELEMENT AND METHOD OF PRODUCING THE SAME

BACKGROUND OF THE INVENTION

1. Field of the Invention

This invention relates to an element for use in detecting an oxygen concentration of gases, and a process for producing the same.

2. Description of the Prior Art

Recently, many attempts have been proposed to provide exhaust gas emission control systems for an automotive internal combustion engine for the purposes of improving the fuel consumption and reducing the amounts of harmful constituents of exhaust gases. It has thus been proposed to detect the oxygen concentration of the exhaust gases and then adjust the flow rate of air or fuel to be fed into the internal combustion engine according to a signal thus detected. The present invention is directed to providing an element for use in detecting the concentration of oxygen contained in gases, such as exhaust gases from an automotive engine.

Various kinds of oxygen concentration detecting elements have been proposed. Among these, a sintered body of an oxide-semiconductor material, such as titanium oxide provides the advantages of simple construction and compact size. However, these detecting elements without exception suffer from a disadvantage in that the detecting elements of oxide-semiconductor type fail to function properly, unless the gases measured are maintained at temperatures as high as about 800° C. (See FIG. 2 showing a comparative example).

Figure 2:
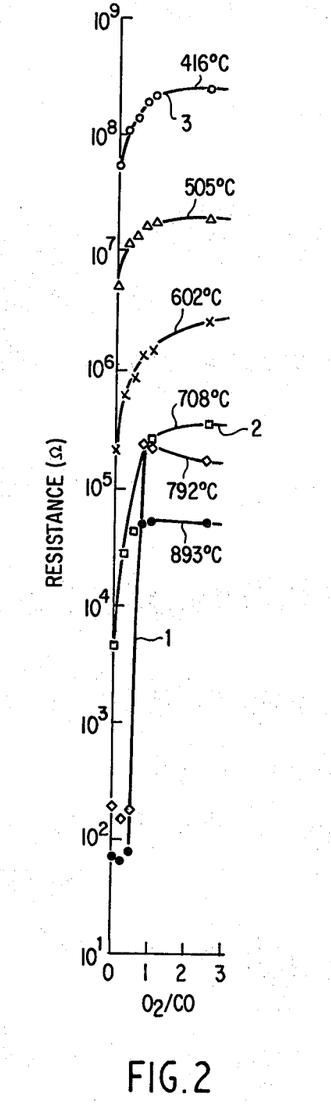
FIG. 2 shows the resistance ratio for a prior-art detection element consisting only of titanium dioxide.

More particularly, in case an oxygen concentration detecting element is used in an exhaust-gas emission control system of an internal combustion engine of the type described above, it is mandatory that the resistance of the detecting element should sharply change in an exhaust gas condition corresponding to a stoichiometric air to fuel ratio, as shown by curve 1 in FIG. 2. The prior art detecting elements of the oxide-semiconductor type merely exhibit slow changes in their resistances for exhaust gases at 700° C. as shown by curve 2, and at 400° C., as shown by curve 3 in FIG. 2. In other words, the use of prior art detecting elements is impossible over a wide temperature range.

Further, the oxygen detecting element should endure both the oxidizing and the reductive atmospheres in the exhaust gas and keep its performance for a long time at elevated temperatures such as above 400° C.

Figure 5:
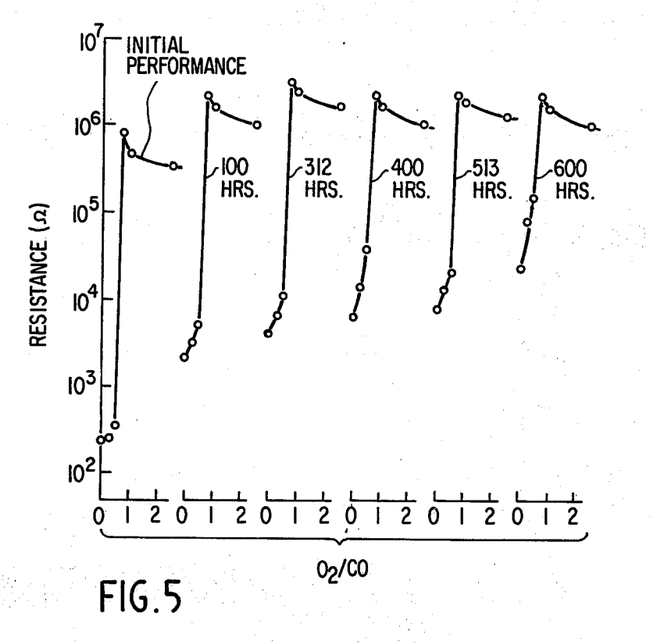
FIG. 5 shows the durability of the resistance ratio for a prior-art platinum-supporting detection element.

To cope with this problem, there has been proposed an oxide-semiconductor type detecting element, in which the surface portion thereof is first permeated with chloroplatinic acid, and then heated, thereby obtaining a platinum-supporting detecting element, in which platinum is supported or carried on the surface portion of the element. The platinum-supporting detecting element, as shown as a comparative example (FIG. 3) in Example 1, enables the use of a wide temperature range but fails to provide practical use during long periods of time, i.e., fails to provide desired durability. (FIG. 5, comparative example, shown in Example 1.)

In standard use, the oxygen concentration detecting element is placed in gases with atmospheric conditions changing alternately from a reductive atmosphere of low oxygen concentration to a highly oxidative atmosphere of high oxygen concentration. It may happen that the oxygen concentration detecting element is exposed to a reductive atmosphere for a long period of time, after which the atmosphere is suddenly replaced by an oxidizing atmosphere. It is necessary in this case as well, that the detecting element rapidly respond or follow the aforesaid change in atmosphere so as to exhibit a change in resistance commensurate with the varying oxygen concentrations. The prior art oxide-semiconductor type detecting elements and their improvements, i.e., platinum-supporting detecting elements, all fail to follow or respond to a rapid or sharp change in oxygen concentration, thus resulting in difficult reproducibility of the resistance. In other words, a hysteresis characteristic results.

SUMMARY OF THE INVENTION

It is an object of the present invention to provide an oxygen concentration detecting element and a process for producing the same.

Another object of the invention is to provide the oxygen concentration detecting element having high durability.

A further object of the invention is to provide the oxygen concentration detecting element having freedom from hysteresis characteristics.

Still a further object of the invention is to provide an oxygen concentration detecting element which can be used over a wide temperature range.

These and other objects of the invention which will become clear hereinafter have been accomplished by providing an oxygen concentration detecting element characterized by a shaped and sintered body, in which oxide-semiconductor materials are mixed with platinum particles in sustantially uniform fashion, in a manner that said platinum particles are dispersed throughout said body at an average particle-to-particle spacing of no more than $10\mu$.

Still more particularly, according to the present invention, there is provided an oxygen concentration detecting element of the type described, in which platinum particles are substantially uniformly dispersed throughout the oxide-semiconductor material at an average particle-to-particle spacing of no more than $10\mu$, with the result that the element affords desired durability in the case of its use for a long period of time at elevated temperatures, is free of hysteresis characteristics, and finds its application over a wide temperature range. In addition, the platinum particles are dispersed throughout the entire shaped body, thus providing the least variation in resistance change per detecting element, and hence consistent or uniform performance and quality.

BRIEF DESCRIPTION OF THE DRAWINGS

FIGS. 1–7 show the embodiments given in Example 1, wherein:

DETAILED DESCRIPTION OF THE PREFERRED EMBODIMENTS

Included in the oxide-semiconductor materials which may be employed in the present invention are titanium oxide, cerium oxide, niobium oxide, tantalum oxide, cobalt oxide, and hafnium oxide. Among these, the former three oxides exhibit a particularly marked change in resistance in response to a change in oxygen concentration, and they are excellent in that they may be stable over wide oxidative and reductive atmosphere ranges.

In addition, the platinum particles are almost uniformly dispersed throughout the oxide-semiconductor material in a minute particulate form, and thus the average particle-to-particle spacing should be no more than $10\mu$. When the spacing is over $10\mu$, the resistance change (resistance ratio) of the element around a stoichiometric air fuel ratio is decreased to below 100 times, thus failing to meet the practicel applications. According to this invention, the smaller the aforesaid spacing, the greater will be the aforesaid resistance change. However, in case the spacing becomes smaller than $0.1\mu$, there results no resistance change commensurate with the value of the spacing thus reduced. For this reason, the aforesaid particle-to-particle spacing should preferably range from 0.1 to $10\mu$. Meant by the terms 'average particle-to-particle spacing', as used herein is an average spacing between each two platinum particles among a plurality of platinum particles dispersed throughout the shaped body. The average particle-to-particle spacing may be determined by scanning the cross-section of a shaped body according to the EPMA analyzing process so as to count the number of platinum particles within a given area of the section, followed by a calculation using the equation given below:

Average particle-to-particle spacing $$R = 2(\sqrt{\frac{X}{\pi}} - \gamma),$$

wherein X represents a value (S/P) obtained by dividing the surface area (S $\mu^2$), in which the number of platinum particles has been counted, by the number (P) of platinum particles; $\pi$ denotes a circular constant (3.14); and $\gamma$ represents the radius ($\mu$) of a platinum particle.

The following is a process for producing the oxygen concentration detecting element which has been thus far described:

Platinum particles of average particle-to-particle spacings of 10 Å to 100 Å are added to the powdered oxide-semiconductor material in a manner that an average particle-to-particle spacing of the platinum particles dispersed throughout the sintered body may be no more than $10\mu$, then the platinum particles and the powdered conductor material are mixed almost uniformly, and molded to a given shape such as a plate or a cylinder, followed by heating at an elevated temperature.

According to the process of the invention, there may be produced in a simple manner an oxygen concentration detecting element which affords excellent performances and high mechanical strength.

The oxide-semiconductor material as used in the present invention is employed in the form of powder, but the diameters of the powder particles are not limitative. However, the diameters of the powder particles should preferably fall in the range of 0.1 to $1\mu$. As a result, a sensitive detecting element is produced since the detecting element thus prepared may provide voids which are well suited for ingress and egress of gases to be detected into or out of the detecting element. The diameters of platinum particles should range from 10 Å to $100\mu$. In case the diameters of the platinum particles is smaller than 10 Å, the platinum particles are too fine, resulting in failure to uniformly mix with the oxide-semiconductor material. On the other hand, in case the diameters are larger than $100\mu$, no improvement in performance of the detecting element is expected while the amount of platinum particles used is increased needlessly. The temperature for heating and sintering the mixture, after molding, should range from 1000° to 1300° C. For preparing a mixture of oxide-semiconductor material with platinum particles in a manner that the average particle-to-particle spacing of the platinum particles may be no more than $10\mu$, for example, platinum particles of diameters ranging from 10 Å to $100\mu$ are added to the oxide-semiconductor material in an amount of 1 to 30% by weight. The platinum particles thus added grow during sintering, so that the diameters of the platinum particles are increased, as compared with those of the platinum particles as originally added. In other words, the amount of the platinum particles to be added should be experimentally determined, taking the above facts into consideration.

Another process for producing a detecting element according to the present invention is such that the surfaces of particles of an oxide-semiconductor material are coated or impregnated with chloroplatinic acid beforehand, and then the material is heated to 100° to 300° C. in a hydrogen atmosphere, followed by heating to 600° to 900° C. in an air atmosphere, thereby preparing particles of oxide-semiconductor material, which surfaces are coated with platinum. Thereafter, the particles of oxide-semiconductor material coated with platinum are molded into a given shape such as a plate or a cylinder and heated and sintered in a manner similar to the foregoing process. During sintering, the platinum on the particles of oxide-semiconductor material grow so as to aggregate.

The detecting element according to the present invention is provided in the form of a porous body, so that the gases to be detected may enter the element with relative ease. In order to measure a change in resistance of the element, lead wires should be connected to it. To this end, two lead wires are connected thereto internally or to the surface thereof at a suitable spacing. (see FIG. 12)

The following examples are illustrative of the features of the present invention, without being limitative thereof unless otherwise specified.

EXAMPLE 1

10% by weight of platinum particles (i.e., platinum black) was added to powdered rutile type titanium oxide serving as an oxide semiconductor material, and these particles were mixed in a wet condition, dried for dehydration, granulated, molded and baked so as to produce an oxygen concentration detecting element.

Figure 12:
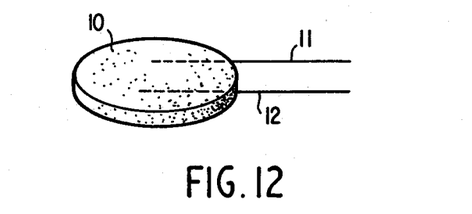
FIG. 12 shows an oxygen concentration detecting element with two lead wires running in parallel through the element.

As shown in FIG. 12, the oxygen concentration detecting element 10 thus produced has two lead wires 11 and 12 running from the interior of the element to the exterior thereof.

In this example, the average diameter of particles of powdered titanium oxide was $1\mu$, while the diameter of particles of platinum black was in the range of 10 Å to several hundred Å. The mixing in a wet condition was carried out by placing agate balls serving as mix-enhancing balls, and water into a polyethylene vessel, followed by agitation for about 10 hours. Drying was carried out by placing the slurry thus obtained from wet-mixing on a tray, and then heating the slurry to about 200° C. The granulation treatment was carried out by adding about 10% by weight of polyvinyl alcohol aqueous solution (about 10% concentration) as a binder to the mixture thus dried, mixing the mixture thoroughly, and then sieving the mixture through a sieve of 150 to 250 mesh. The molding was carried out by placing the particles thus granulated into a permanent mold, with the tips of two platinum wires serving as the lead wires being placed on top of the particles thus granulated, followed by molding under a pressure of about 800 kg/cm². As referred to in FIG. 12, the body thus molded was of a disc form, which was 4 mm in diameter and 0.6 mm in thickness, with two lead wires 11 and 12 running from the interior of the body to the exterior thereof. The diameter of the lead wires 11 and 12 was 0.3 mm, and the end portions of the lead wires were placed at a spacing of about 1 mm in parallel with each other in the interior of the molded body. The molded body was then placed in a heating oven in an air atmosphere, with the temperature being increased at a rate of 266° C./hour, after which the body was maintained at about 1100° C. for 3 hours, followed by slow cooling.

The oxygen concentration detecting element thus sintered had a density of about 2.6 g/cm³, voids of a diameter of about $0.3\mu$, and a porosity of about 38%. In addition, the diameter of titanium oxide particles was about $2\mu$, and the diameters of platinum particles ranged from about 0.1 to $0.3\mu$ due to growth during the sintering (according to EPMA analyzing procedure). Further the particle-to-particle spacing of platinum particles was found to be $3.1\mu$.

The following characteristics of the detecting element thus obtained were measured.

(1) Change in resistance(resistance ratio) of the element in response to oxygen concentration.

Figure 1:
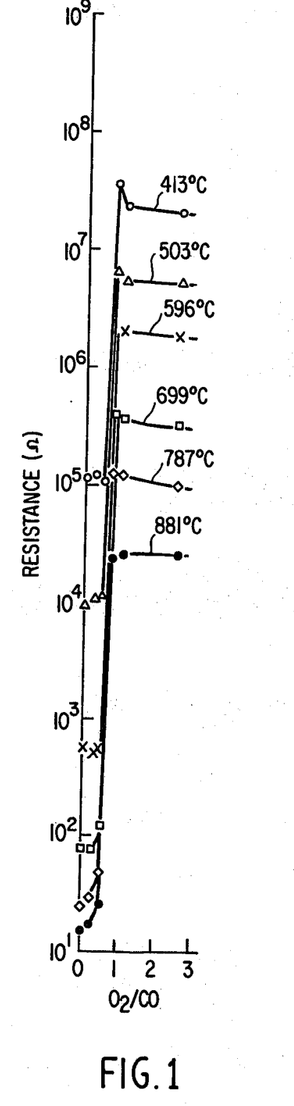
FIG. 1 shows the change in resistance (resistance ratio) of a titanium dioxide detection element of the present invention in response to oxygen concentration.

A detecting element was placed in gases to be measured, while the oxygen concentration (in said gases) was varied at temperatures of from 400° to 900° C. The resistances of the detecting elements were measured at varying temperatures and oxygen concentrations. FIG. 1 shows the results of these measurements, with the abscissa representing oxygen concentration ($O_2/CO$) of gases to be measured, and with the ordinate representing resistances ($\Omega$) of the element. These measurements were taken at various gas temperatures. Like marks or symbols shown represent like gas temperatures, respectively.

Typically the oxygen concentration of gases to be measured was adjusted in the following manner. A mixture gas consisting of 2% by volume of carbon monoxide gas and 98% by volume of nitrogen gas was fed at a flow rate of 1.5 l/min into a tubular electric furnace, in which the detecting element was placed, and then the oxygen concentration was adjusted by feeding oxygen gas into the gas mixture at a flow rate of 0 to 50 ml. The feeding or supply of oxygen gas at a rate of 10 ml/min, corresponds to the oxygen concentration of exhaust gases resulting, when an automotive internal combustion engine is run at a stoichiometric air to fuel ratio. In case the oxygen concentration detecting element is used as an element (oxygen sensor) for detecting the oxygen concentration of exhaust gases, of the aforesaid exhaust gas emission control systems for an automotive internal combustion engine, it is mandatory that the resistance of the detecting element sharply or rapidly change in the neighborhood of the stoichiometric air to fuel ratio.

The reason why, as shown in FIG. 1, the oxygen concentrations of gases to be measured are represented by a ratio in amount of oxygen ($O_2$) to carbon monoxide ($CO$), is for the convenience of evaluation of the element as an oxygen sensor. Table 1 shows the relationship between the ratio '$O_2/CO$' and the oxygen concentrations (%) of gases to be measured. In this respect, $O_2/CO=0.5$ corresponds to the gas concentration equivalent to the aforementioned stoichiometric air to fuel ratio.

TABLE 1

| $O_2/CO$ ratio | 0 | 0.2 | 0.4 | 0.6 | 0.8 | 1.0 | 1.5 | 2.0 | 3.0 | 4.0 |
|---|---|---|---|---|---|---|---|---|---|---|
| oxygen concentration (%) of gases to be measured | 0 | 0.4 | 0.8 | 1.2 | 1.6 | 2.0 | 3.0 | 4 | 6 | 8 |

As can be seen from FIG. 1, the detecting element according to the present invention exhibits a sharp change in resistance in the gas compositions equivalent to those having a stoichiometric air to fuel ratio. The resistance ratios of the element are $3.16 \times 10^2$ at 413° C., $4.55 \times 10^3$ at 596° C., and $1.48 \times 10^3$ at 881° C., presenting extremely high resistance ratios. From this data it can be deduced that the detecting element according to the present invention is excellent. Meant by the term "resistance ratio" as used herein is a quotient ($R_1/R_2$) of the resistance $R_1$ at high oxygen concentration, divided by the resistance $R_2$ at low oxygen concentration. In this respect, the value of resistance $R_1$ adopts the value of the resistance on the condition that the ratio $O_2/CO$ is 0, while the resistance $R_2$ adopts the value of the resistance on the condition that the ratio $O_2/CO$ is 0.75.

For comparison purposes, a prior art oxide-semiconductor material consisting merely of titanium oxide was produced in the absence of platinum particles in a manner similar to the production process as given in the example of the present invention. The relationship between the oxygen concentration $O_2/CO$ and the resistance ratio was then measured at various temperatures. This detecting element provides almost the same density, void diameter, porosity and like as those of the element given in the example, except for the absence of platinum particles.

FIG. 2 shows the result of measurements obtained in a manner similar to those of FIG. 1, but with the comparative element.

As can be seen from FIG. 2, the resistance ratios of the prior art detecting element without platinum are 1.98 at a temperature of 416° C., 4.73 at 602° C., and $7.15 \times 10^2$ at 893° C. The temperature at which the aforesaid ratio exceeds 100 times is over about 700° C. Thus, it can be seen from this that the detecting element of the prior art is not suited for practical applications at temperatures below 700° C. In contrast thereto, the element according to the present invention may be employed even at 400° C.

For comparison purposes, measurements similar to those in the example were made with a prior art oxide-semiconductor type detecting element, which has been impregnated with platinum, (platinum-supporting detecting element). This detecting element was prepared by dipping the oxide-semiconductor type detecting element shown in the foregoing comparative example into an aqueous solution of 10% by weight of chloroplatinic acid, and then taken out from the solution and dried. The above procedure was repeated three times, and then the element was heated to 800° C., so as to have platinum supported on the surface of the element.

Figure 3:
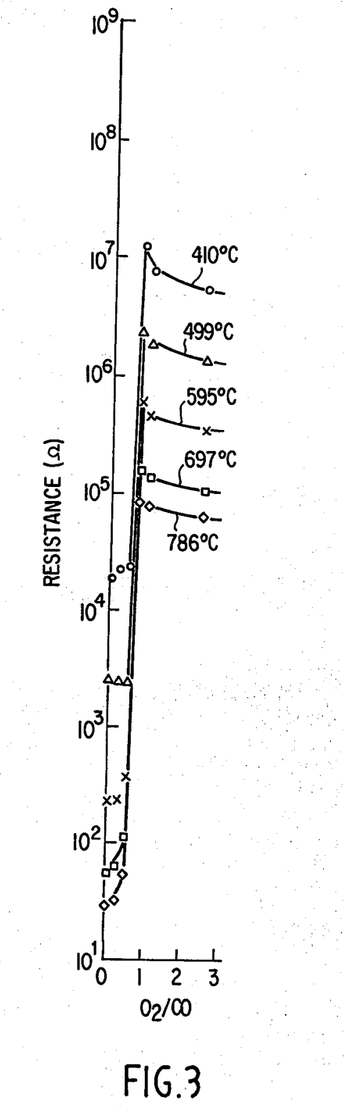
FIG. 3 shows the resistance ratio for a prior-art detection element consisting of a platinum-supporting element.

FIG. 3 shows the results of measurements in the same manner as in FIG. 1, but with the Pt-supporting comparative element.

As can be seen from FIG. 3, the resistance ratios of the prior art detecting element are $9.45 \times 10^2$ at 410° C., $2.56 \times 10^3$ at 595° C., and $3.04 \times 10^3$ at 786° C. As is clear from this, the detecting element according to the present invention affords similar characteristics to those of a prior art platinum-supporting detecting element, as far as the resistance ratio is concerned.

Figure 4:
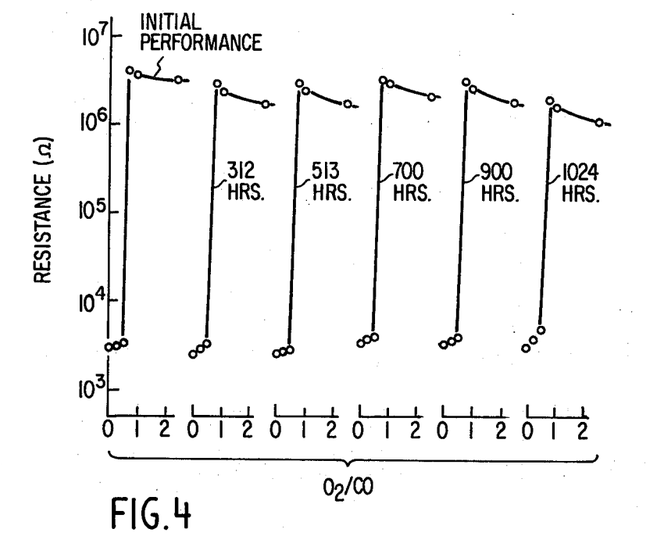
FIG. 4 shows the durability of the resistance ratio for the titanium oxide detection element of the present invention.

(2) Durability:

The durability of the detecting element having an average particle-to-particle spacing of $3.1\mu$ of platinum according to the present invention was measured at elevated temperatures. In this case, the detecting element was placed in gases to be measured, at 590° to 605° C., and then the resistances of the element were measured at various oxygen concentrations of the gases at various time intervals. FIG. 4 shows the results of the measurements given at various intervals, in a manner similar to that of FIG. 1. The time for each measurement is shown therein.

As can be seen from FIG. 4, the initial performance of a detecting element according to the present invention changes little after its exposure to gases for 1024 hours.

Similar measurements were taken for the foregoing platinum-supporting detecting element for comparison purposes. FIG. 5 shows the results of the measurements. As can be seen from FIG. 5, the platinum-supporting element having its surface impregnated with platinum alone shows no marked change in resistance at higher oxygen concentrations, after an exposure for 100 hours; the resistance of the element at lower oxygen concentrations however, is increased with time, and the resistance ratio is thus lowered with time, proving poor durability. In addition, the resistance ratio of the prior-art element after 600 hours is lowered to below 100 times, affording difficulty in the practical application.

(3) Hysteresis characteristics:

The detecting element produced according to the present invention was placed in an atmosphere maintained under condition A of Table 2, and the resistance of the element was then measured. Thereafter, the element thus tested was placed in an atmosphere as defined by condition B, and the resistance of the element was then measured. The hysteresis characteristic of the element was then measured by comparing the former measurement with the latter. In this respect, the element was exposed for a long period of time to gases containing carbon monoxide in condition A and to gases containing oxygen in condition B respectively.

TABLE 2

|  | Condition A | Condition B |
|---|---|---|
| Composition of gases | a gas mixture of nitrogen gas fed at a rate of 1.2 l/min. and carbon monoxide gas fed at a rate of 20ml/min. | a gas mizture of nitogen gas fed at a rate of 1 l/min and oxygen gas fed at a rate of 50 ml/min. |
| Temperature | 777° C. | 777° C. |
| Exposure duration | 3 hours | 3 hours |

Figures 6A, 6B, 6C:
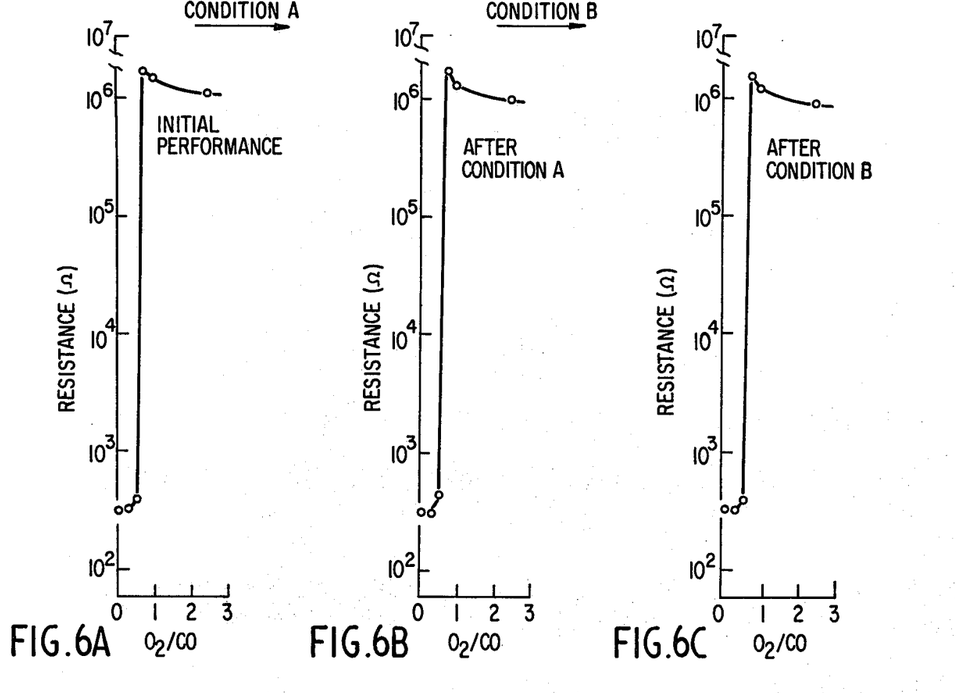
FIG. 6 shows the hysteresis characteristics for the titanium dioxide detection element of the present invention.

The results of these measurements are shown in FIG. 6 in a manner similar to FIG. 1, in terms of the resistances of the detecting element at the initial stage, under condition A and then under condition B. The measurements taken at the various points were made at a temperature of 590° C.

The resistances of the elements after exposure to conditions A and B were found to be substantially the same thus proving freedom from a hysteresis effect.

Figures 7A, 7B, 7C:
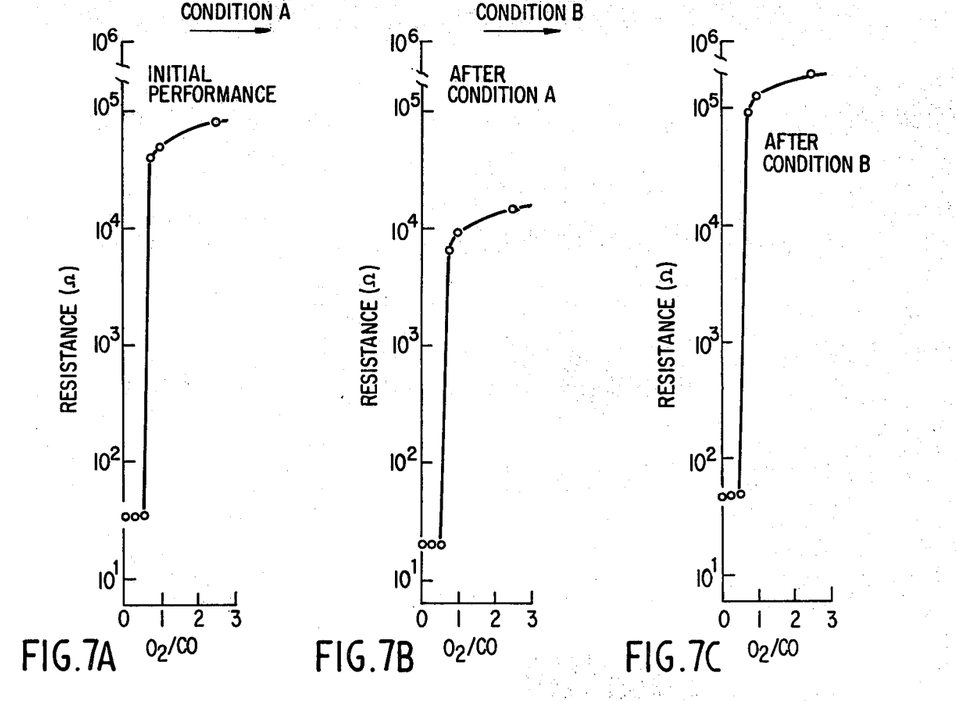
FIG. 7 shows the hysteresis characteristics for a prior-art platinum supporting detection element.

Similar measurements were taken for the aforementioned platinum-supporting detecting element for comparison purposes. The results of the measurements are shown in FIG. 7 in a manner similar to that of FIG. 6. The measurements at various points were taken at a temperature of 579° C.

As can be seen from FIG. 7, the resistance of the prior art platinum-supporting detecting element in an atmosphere containing a high oxygen concentration is decreased after its exposure to condition A, while the resistance of the element is sharply increased after exposure to condition B. This proves that the prior art detecting element shows marked hysteresis characteristics.

As is apparent from the description given under paragraphs (1) through (3), the oxygen concentration detecting element of the present invention exhibits a high resistance ratio over a wide range of temperatures, excellent durability, in addition to the freedom from hysteresis characteristics.

EXAMPLE 2

Detecting elements having various particle-to-particle spacings were produced, and the resistance ratios of the detecting elements were then measured.

More particularly, rutile type titanium oxide powder was used as an oxide-semiconductor material as in Example 1, and platinum particles of diameters as shown in Table 3 were then added at ratios shown therein, followed by mixing in a wet condition, drying for dehydration, granulation, molding and baking or sintering, in a manner similar to that of Example 1. The detecting elements afford densities after sintering, of 2.3 to 3.0 g/cm³, voids of diameters of 0.3 to 1.7μ, and ratio of pores of 30 to 45%. In addition, the diameters of titanium oxide particles were found to range from 1 to 4μ, and the platinum particles, in cases where platinum black was added, grew to provide diameters of 0.1 to 0.3μ, after sintering. Further, samples (Nos. 7 to 9) to which platinum powder was added did not exhibit marked growth of particles after sintering.

The resistance ratios of the detecting elements were thus obtained in a manner similar to that of Example 1(1), at various oxygen concentrations at a temperature of 400° C. The results of these measurements are shown in Table 3 along with the particle-to-particle spacing of platinum particles contained in the detecting elements, and types and amounts of the platinum added.

As can be seen from Table 3, the detecting elements (sample Nos. 1 to 5, 7, 8) having average particle-to-particle spacings of no more than 10μ according to the present invention exhibited resistance ratios of no less than 100, although the elements having spacings exceeding the above range exhibited low-resistance ratios. It is apparent that the above fact has no bearing on the types and amounts of platinums used in the initial stage of production. (For instance, see sample Nos. 3 and 9 having almost the same amount of platinum added, while the types of platinum are different).

TABLE 3

| Sample No. | 1 | 2 | 3 | 4 | 5 | 6 | 7 | 8 | 9 |
|---|---|---|---|---|---|---|---|---|---|
| Average particle-to-particle spacing of platinum (u) | 1.2 | 3.1 | 4.3 | 6 | 9 | 13 | 1.5 | 9.2 | 18 |
| Types of platinum added | Platinum black of diameters of 10 A to several hundreds A | | | | | | Platinum particles of diameters of 0.1 to 63μ. | | |
| Amount of platinum added (Wt %) | 20 | 10 | 6 | 3 | 1 | 0.5 | 30 | 10 | 5 |
| Resistance ratios (times) | 1300 | 1300 | 990 | 500 | 100 | 13 | 1200 | 110 | 12 |
| | Present invention | | | | | Comp. example | present invention | | Comparative example |

EXAMPLE 3

Powdered cerium oxide ($CeO_2$) of average particle diameter of 1μ was used as an oxide-semiconductor material, and then 10% by weight of platinum black as shown in Example 1 was added thereto. Detecting elements of a diameter of 4 mm, and a thickness of 0.5 mm were then produced in a manner similar to that of Example 1. The average particle-to-particle spacing of platinum in this example was 3.1μ.

Figure 8:
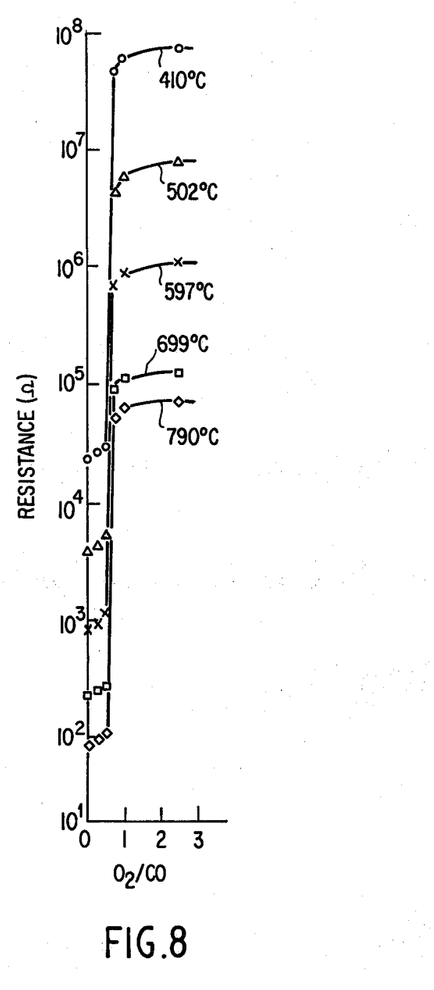
FIG. 8 shows the resistance ratio for a cerium oxide detection element of the present invention.
Figure 9:
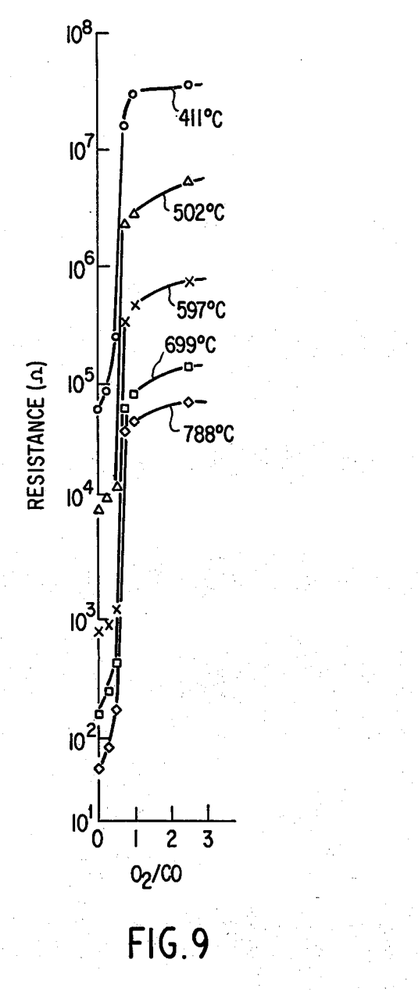
FIG. 9 shows the resistance ratios for a prior-art detection element consisting only of cerium oxide.

Changes in resistance of the detecting elements due to varying oxygen-concentrations were measured as in the case of Example 1. The results of measurements are shown in FIG. 8 in a manner similar to that of FIG. 1. For comparison purposes, detecting elements containing cerium oxide alone were produced without adding platinum, while all procedures were followed in the same manner as that of the preceding examples. The changes in resistance of the detecting elements due to varying oxygen concentrations were then measured. FIG. 9 shows the results of measurements in the same manner as FIG. 1.

As is apparent from FIGS. 8 and 9, the detecting elements produced according to the present invention show excellent resistance ratios over a wide temperature range (FIG. 8).

EXAMPLE 4

Powdered niobium oxide ($Nb_2O_5$) of an average particle diameter of 1μ was used as an oxide-semiconductor material and then 10% by weight of platinum black as used in Example 1 was added thereto, so that detecting elements of a diameter of 4 mm, and a thickness of 0.5 mm were produced in a manner similar to that of Example 1. The average particle-to-particle spacing of the platinum particles was 3.1μ.

Figure 10:
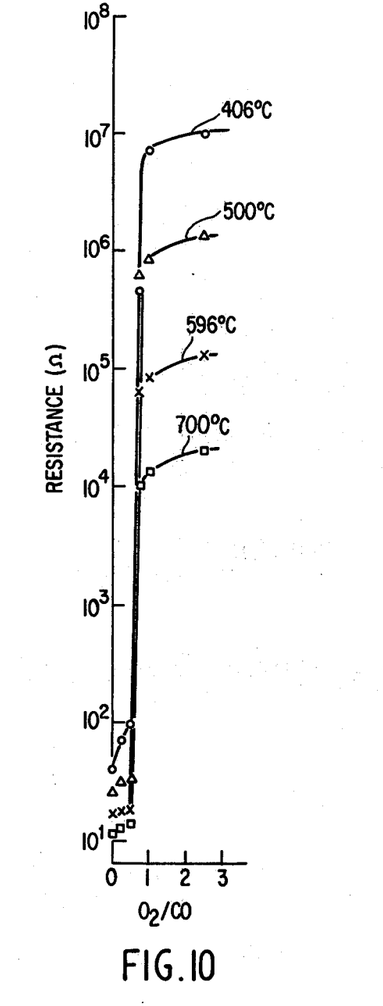
FIG. 10 shows the resistance ratios for a niobium oxide detection element of the present invention.

Changes in resistance due to varying oxygen concentrations of the detecting elements thus prepared were measured, and the results are shown in FIG. 10 in a manner similar to that of FIG. 1.

Figure 11:
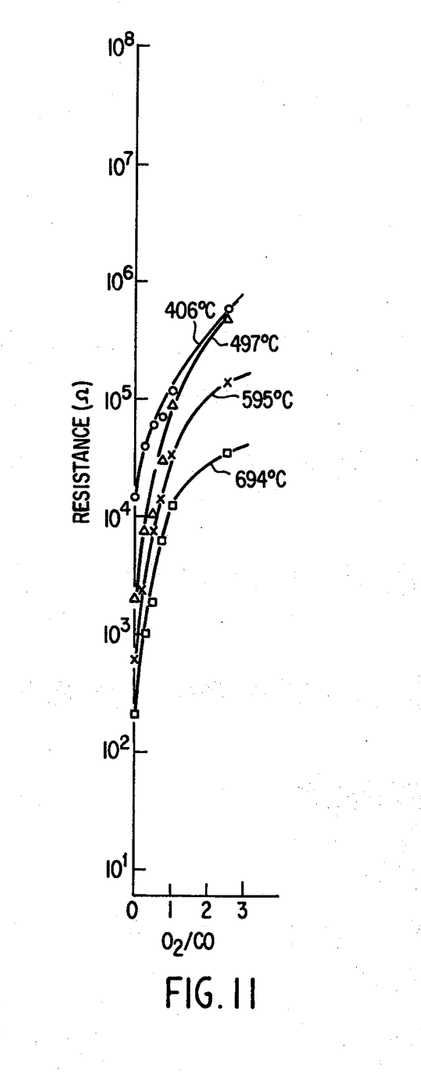
FIG. 11 shows the resistance ratio for a prior-art detection element consisting only of niobium oxide.

For comparison purposes, detecting elements containing niobium oxide alone were produced, without adding platinum, and measurements then were taken, following the foregoing procedure. FIG. 11 shows the results of the measurements as in the case of FIG. 1.

As can be seen from FIGS. 10, 11, the detecting elements produced according to the present invention (FIG. 10) exhibit excellent resistance ratios over a wide temperature range, and give a resistance ratio as high as $10^5$ even at a temperature as low as 406° C., thus providing excellent performance. On the other hand, the detecting elements including niobium oxide alone were found to be defective as the oxygen concentration detecting element.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An oxygen concentration detecting element which is an electrical resistance element for the detection of oxygen concentration in the exhaust gases of internal combustion engines comprising a shaped molded and sintered porous body consisting essentially 70 to 99 weight percent of oxide-semiconductor material selected from the group consisting of titanium oxide, cerium oxide, niobium oxide, tantalum oxide, cobalt oxide and hafnium oxide and 1 to 30 weight percent of platinum particles sintered together with the powder form of said oxide semiconductor material, said platinum particles being dispersed substantially uniformly throughout said porous body thus obtained at an average particle-to-particle spacing of 0.1μ to 10μ, said element being so designed that a change in the resistance of the sintered porous body due to a change in oxygen concentration of gases in which the element is placed may be measured.

2. An oxygen concentration detecting element according to claim 1, wherein said oxide-semiconductor material is titanium oxide.

3. An oxygen concentration detecting element according to claim 1, wherein said oxide-semiconductor material is cerium oxide.

4. An oxygen concentration detecting element according to claim 1, wherein said oxide-semiconductor material is niobium oxide.

5. An oxygen concentration detecting element according to claim 1, wherein
said oxide-semiconductor material is selected from the group consisting of tantalum oxide, cobalt oxide, and hafnium oxide.

6. An oxygen concentration detecting resistance element according to claim 1 wherein said molded and sintered porous body has lead wires connected thereto.

7. An element according to claim 6 which exhibits a sharp range in resistance at about the stoichiometric air to fuel ratio over a range of temperatures of about 400° to 900° C.

8. An element according to claim 1 wherein the platinum particles in the sintered body are characterized by a diameter substantially in the range of 0.1 to 0.3μ.

9. A process for producing an oxygen concentration detecting element which is an electrical resistance element comprising the steps of:
mixing 1–30% by weight of platinum particles of average diameters falling within the range of 10 Å to 100μ and 70 to 99% by weight of powdered oxide-semiconductor material selected from the group consisting titanium oxide, cerium oxide, niobium oxide, tantalum oxide, cobalt oxide, and hafnium oxide,
press molding the mixture thus prepared into a given shape; and
heating and sintering the thus shaped body at an elevated temperature in air until a particle to particle spacing of platinum particle in the range of 0.1 to 10μ is obtained.

10. A process for producing an oxygen concentration detecting element according to claim 9, wherein said oxide-semiconductor material is titanium oxide.

11. A process for producing an oxygen concentration detecting element according to claim 9, wherein said oxide-semiconductor material is cerium oxide.

12. A process for producing an oxygen concentration detecting element according to claim 9, wherein said oxide-semiconductor material is niobium oxide.

13. A process for producing an oxygen concentration detecting element according to claim 9, wherein said oxide-semiconductor material is selected from the group consisting of tantalum oxide, cobalt oxide, and hafnium oxide.

14. A process for producing an oxygen concentration detecting element according to claim 9, wherein the average diameter of said powdered oxide-semiconductor material is in a range of 0.1 to 1μ.

15. A process for producing an oxygen concentration detecting element according to claim 14, wherein said thus shaped body is sintered at temperatures as high as 1000° C. to 1300° C.

16. A process according to claim 9 wherein the platinum particles mixed with the powdered oxide-semiconductor material is platinum black and the diameters of the platinum particles in the sintered body falls in the range of about 0.1 to 0.3μ.

17. A process for producing an oxygen concentration detecting element which is an electrical resistance element comprising the steps of:
feeding the particles of oxide-semiconductor material coated with 1–30% by weight of platinum into a mold;
molding said particles into a given shape; and then heating and sintering in air the thus shaped body into a porous body, at an elevated temperature of 1000° to 1300° C. until a particle to particle spacing of platinum particles within the range of 0.1μ to 10μ is obtained, the oxide-semiconductor material being selected from the group consisting of titanium oxide, cerium oxide, niobium oxide, tantalum oxide, cobalt oxide and hafnium oxide.

* * * * *